United States Patent
Kohler

(10) Patent No.: US 9,080,707 B2
(45) Date of Patent: Jul. 14, 2015

(54) INTELLIGENT CONTRAST WARMER AND CONTRAST HOLDER

(71) Applicant: MEDRAD, INC., Indianola, PA (US)

(72) Inventor: Bernhard D. Kohler, Euclid, OH (US)

(73) Assignee: Bayer Medical Care Inc., Indianola, PA (US)

(*) Notice: Subject to any disclaimer, the term of this patent is extended or adjusted under 35 U.S.C. 154(b) by 118 days.

(21) Appl. No.: 13/765,467

(22) Filed: Feb. 12, 2013

(65) Prior Publication Data

US 2014/0224784 A1     Aug. 14, 2014

(51) Int. Cl.
*A21B 1/00* (2006.01)
*F16L 53/00* (2006.01)
*G08B 29/00* (2006.01)

(52) U.S. Cl.
CPC ...................... *F16L 53/00* (2013.01)

(58) Field of Classification Search
USPC ............... 219/400, 433; 340/584, 540, 5.73, 340/572.1
See application file for complete search history.

(56) References Cited

U.S. PATENT DOCUMENTS

| | | | |
|---|---|---|---|
| 1,717,132 | A | 6/1929 | Weinmann |
| 2,500,241 | A | 3/1950 | Brown |
| 2,526,447 | A | 10/1950 | Aiken |
| 5,451,528 | A | 9/1995 | Raymoure et al. |
| 5,786,573 | A | 7/1998 | Fabrikant et al. |
| 6,575,906 | B1 | 6/2003 | Schembri, Jr. et al. |
| 7,128,105 | B2 | 10/2006 | Tribble et al. |
| 7,264,148 | B2 | 9/2007 | Tachibana |
| 7,728,711 | B2 * | 6/2010 | Shoenfeld ............. 340/5.73 |
| 2005/0203329 | A1 | 9/2005 | Muto et al. |
| 2008/0147014 | A1 | 6/2008 | Lafferty |
| 2008/0211674 | A1 * | 9/2008 | Gibson et al. .............. 340/572.1 |
| 2011/0307117 | A1 | 12/2011 | McKinnon et al. |
| 2012/0330152 | A1 | 12/2012 | Reisinger et al. |

FOREIGN PATENT DOCUMENTS

| | | |
|---|---|---|
| WO | 9910027 A1 | 3/1999 |
| WO | 2004091688 A2 | 10/2004 |
| WO | 2006083359 A2 | 8/2006 |
| WO | 2007033103 A1 | 3/2007 |
| WO | 2008076631 A2 | 6/2008 |

OTHER PUBLICATIONS

The International Search Report and Written Opinion mailed Aug. 7, 2014 from corresponding PCT Application No. PCT/US2014/015507.
International Search Report and Written Opinion for International Patent Application No. PCT/EP2010/068097 mailed May 19, 2011.

* cited by examiner

*Primary Examiner* — Shawntina Fuqua
(74) *Attorney, Agent, or Firm* — James R. Stevenson; Bojan Popovich; Joseph T. Helmsen

(57) ABSTRACT

Intelligent contrast warmers and methods for operating and using same are described. An intelligent contrast warmer may include elements configured to monitor information associated with the intelligent contrast warmer and contrast media stored in contrast bottles housed within the intelligent contrast warmer, such as contrast warmer temperatures, contrast warmer temperatures outside of specifications, contrast media inventory, expiration dates of contrast media, personnel authorized to access contrast media, and dates and times associated with contrast media added to and removed from the intelligent contrast warmer. A method for monitoring the expiration date of contrast bottles may include labeling the contrast bottles and reading the information from the label into a computing device. The computing device may be configured to monitor the expiration dates and to generate an alarm responsive to a current time being within a threshold duration of the expiration time for a contrast bottle.

18 Claims, 8 Drawing Sheets

INTELLIGENT CONTRAST WARMER AND CONTRAST HOLDER

BACKGROUND

Contrast media are administered to patients to enhance the contrast of bodily structures or fluids during certain medical procedures. For example, contrast media are used in diagnostic imaging procedures, including X-ray, computed tomography (CT), magnetic resonance imaging (MRI), and ultrasound, and in interventional radiological procedures, such as angioplasty and certain types of chemotherapy. Various forms and concentrations of contrast media are available and are selected based on the type of procedure and the subject of interest. Illustrative contrast media include barium- and iodine-based solutions commonly used in radiological imaging procedures. Contrast media may be delivered to patients through various methods, including ingestion, manual injections, or automated fluid delivery systems (e.g., syringe pumping systems).

Certain types of contrast media are warmed in a heated incubator, commonly called a contrast warmer, to bring the contrast media to a temperature and viscosity closer to that of blood. Manufacturer recommendations and regulatory standards of care must be followed when storing and warming contrast media. For example, the Joint Commission on Accreditation of Healthcare Organizations (the "Joint Commission" or "TJC"), the accrediting body most commonly used by hospitals in the United States, provides the following set of standards for warming contrast media:

Contrast media warmer temperatures should be established according to the manufacturer's recommendations. Daily monitoring and documentation of warmer temperatures is required, and the appropriate threshold for corrective action must be indicated on the documentation log. Warmers whose temperatures exceed threshold limits must have corrective action documented and should be rechecked in 1 hour to ensure actions have been effective. Staff should be aware that expiration dates may change with warming. Contrast agents typically are stable for 30 days with warming.

Other standards are also applicable to the storing and warming of contrast media. For instance, TX standards also specify guidelines for limiting access to contrast media to authorized personnel.

In general, conventional contrast warmers maintain temperatures using traditional thermostatic elements and digital temperature displays. As such, they only provide the ability to set a desired temperature. In addition, access to contrast media is secured using basic mechanical locking mechanisms. Accordingly, storing and warming contrast media according to regulatory standards of care is a manual and labor intensive process. Ultimately, the time and effort expended on properly storing and warming contrast media takes away resources that would otherwise be used to provide quality patient care.

SUMMARY OF THE INVENTION

In one aspect, some embodiments provide an intelligent contrast warmer including elements configured to monitor information associated with the intelligent contrast warmer and contrast media stored in contrast bottles housed within the intelligent contrast warmer. Non-limiting examples of such information include contrast warmer temperatures, contrast warmer temperatures outside of specifications, contrast media inventory, expiration dates of contrast media, personnel authorized to access contrast media, and dates and times associated with contrast media added to and removed from the intelligent contrast warmer.

In another aspect, some embodiments include an intelligent contrast warmer communicatively coupled with a display device configured to present an intelligent contrast warmer user interface. The intelligent contrast warmer user interface may operate to provide user access to the intelligent contrast warmer and information associated therewith. For example, the intelligent contrast warmer user interface may be used to provide a username and password to lock/unlock the intelligent contrast warmer, add contrast bottles to the intelligent contrast warmer, and remove bottles from the intelligent contrast warmer.

In a further aspect, some embodiments include one or more contrast labels for labeling the contrast bottles and one or more information readers configured to obtain information associated with the one or more contrast labels. For example, a contrast label may be labeled with one or more of the following types of contrast labels: text-based, radio frequency identification (RFID), barcode, and quick response (QR) code. An information reader may be used to read a contrast label. For instance, one or more of the following information readers may be used to read information included in a contrast label of a corresponding type: an optical character recognition (OCR) reader, RFID reader, barcode reader, and QR code reader. In an embodiment, the contrast label reader may be in communication with the intelligent contrast warmer and/or aspects thereof, including a display device or computing device. In this manner, information associated with a contrast label may be transmitted to the intelligent contrast warmer and/or systems associated therewith.

In a still further aspect, some embodiments provide that the intelligent contrast warmer, the intelligent contrast warmer user interface, display device, and/or computing devices associated with the intelligent contrast warmer may be in communication with an intelligent contrast warmer system. The intelligent contrast warmer system may be configured according to some embodiments to manage information associated with the intelligent contrast warmer and the contrast bottles stored therein. For example, the intelligent contrast warmer system may maintain information including one or more of the following: contrast bottles added and removed from the intelligent contrast warmer; personnel, dates, and times associated with bottles added and removed from the intelligent contrast warmer; incidences of temperatures outside of specification; contrast bottle expiration dates; and contrast bottle inventory. In this manner, personnel may obtain information concerning the intelligent contrast warmer and the contrast bottles stored in the intelligent contrast warmer from a central access point.

In an embodiment, a contrast warmer may be operative to monitor a temperature of a storage space arranged therein to store contrast bottles and to generate an alarm responsive to the temperature being outside of an acceptable temperature range, wherein information associated with the alarm is stored in a database on at least one computing device.

In an embodiment, a contrast warmer may comprise an information reader operative to read contrast information of a contrast label affixed to a contrast bottle, the contrast information comprising an expiration time, wherein a computing device in communication with the information reader is configured to receive the contrast information and to generate an alarm event responsive to a current time being within a threshold duration of the expiration time.

In an embodiment, a contrast warmer configured to warm contrast bottles stored therein may comprise: a temperature sensor operative to measure a temperature of the contrast warmer; and a communications port in operative communication with at least one computing device configured to monitor the temperature, wherein an alarm event is generated by the at least one computing device responsive to the temperature being outside of an acceptable temperature range.

In an embodiment, a method of monitoring an expiration time of a contrast bottle stored in a contrast warmer may comprise: affixing a contrast label to the contrast bottle, the contrast label comprising the expiration time of the contrast bottle; reading the expiration time from the contrast label using an information reader; placing the contrast bottle in the contrast warmer; communicating the expiration time from the reader to at least one computing device configured to receive the expiration time; and generating, by the at least one computing device, an alarm event responsive to a current time being within a threshold duration of the expiration time.

In an embodiment, a contrast warmer system may comprise: a fluid injector configured to inject contents of a contrast bottle into a patient; a contrast holder comprising: a heating element configured to store and warm the contrast bottle; an information reader configured to read information from a contrast label having contrast information, the contrast label being affixed to the contrast bottle; a communication port configured to provide communication with at least one computing device, wherein the contrast holder is in fluid communication with the fluid injector.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this document is to be construed as an admission that the embodiments described in this document are not entitled to antedate such disclosure by virtue of prior invention.

This disclosure is not limited to the particular systems, devices and methods described, as these may vary. The terminology used in the description is for the purpose of describing the particular versions or embodiments only, and is not intended to limit the scope.

The present disclosure is directed toward an intelligent contrast warmer system. The intelligent contrast warmer system includes a contrast warmer for warming contrast media stored in bottles communicatively connected to one or more electronic devices configured to receive, transmit, and/or manage information associated with the intelligent contrast warmer and contrast media stored therein. Illustrative and non-restrictive examples of the electronic devices include computing devices, printers, networks, display devices, and/or information readers. The intelligent contrast warmer system may be configured to provide information, access, and alerts associated with the contrast warmer, contrast media, and the intelligent contrast warmer system. For example, the intelligent contrast warmer system may provide information such as contrast inventory, contrast information, and contrast expiration dates. The intelligent contrast warmer system may also provide system alerts, such as temperature out-of-range conditions, expired contrast media and contrast media nearing expiration, low inventory conditions, and unauthorized access attempts. Users may manage the contrast warmer and contrast media through contrast functions. According to some embodiments, contrast functions may include adding contrast to the contrast warmer, removing contrast media from the contrast warmer, temperature control, and information transmission to other information systems (e.g., picture archiving and communication system (PACS)).

Figure 1:
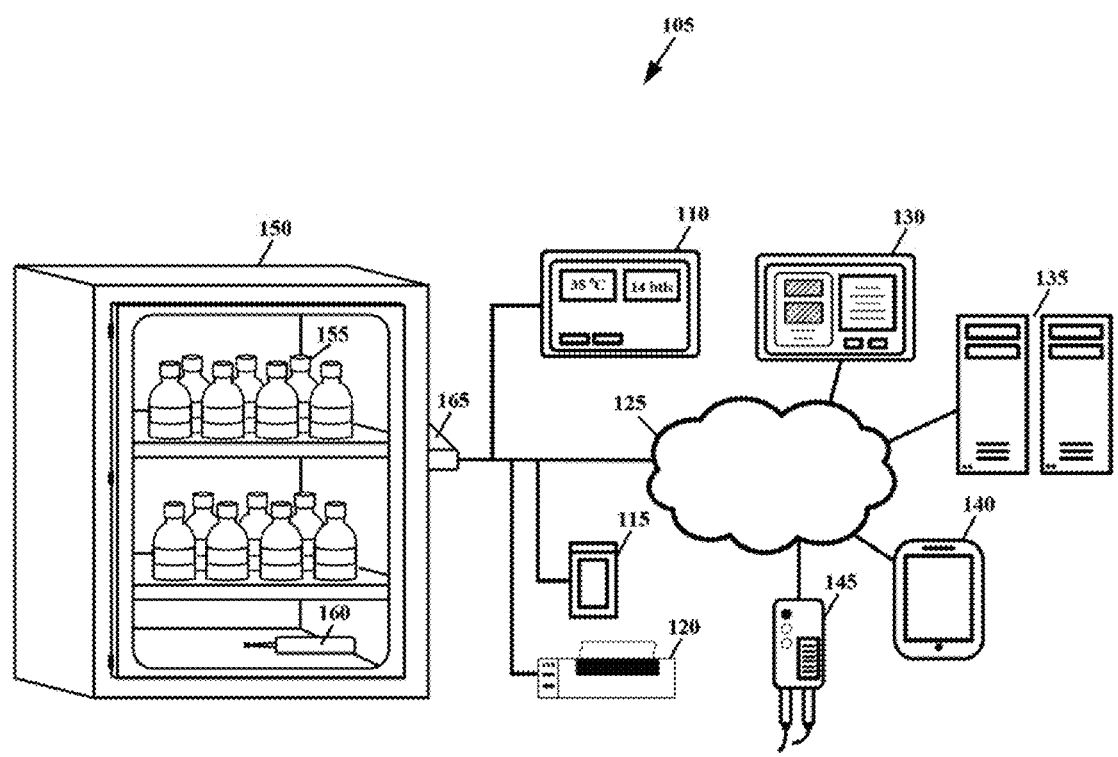
FIG. 1 depicts an illustrative intelligent contrast warmer system according to some embodiments.
Figure 2:
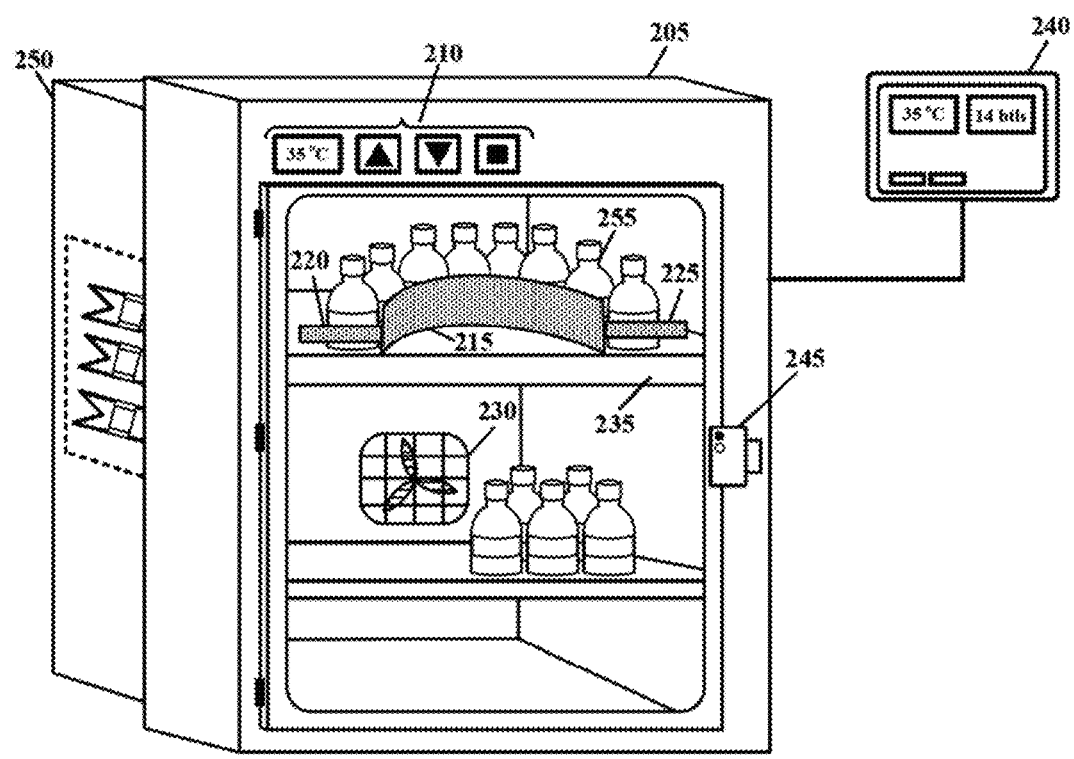
FIG. 2 depicts an illustrative intelligent contrast warmer configured according to some embodiments.

FIG. 1 depicts an illustrative intelligent contrast warmer system according to some embodiments. As shown in FIG. 1, an intelligent contrast warmer system 105 may include a contrast warmer 150 configured to maintain the temperature of contrast bottles 155 stored therein. A non-limiting example provides that the temperature may be controlled at about 35° C. to about 37° C. to maintain the contrast media stored in the contrast bottles 155 at a temperature and viscosity approximate to blood in the human body. The temperature may be measured and/or monitored by one or more temperature sensors 160. FIG. 2, described below, provides more detail of a contrast warmer configured according to some embodiments.

The contrast warmer 150 may be connected to one or more networks 125 and/or one or more electronic devices 110, 115, 120 through one or more communication ports 165 according to known communication methods. Illustrative and non-limiting examples of communication methods available through the communication ports 165 include Ethernet, wireless protocols (e.g., WiFi 802.11g, 802.11n, etc.) serial, universal serial bus (USB), parallel port, Bluetooth®, proprietary device protocols (e.g., for barcode reader, RFID readers, QR code readers, temperature sensors, etc.). For instance, the contrast warmer 150 may be connected to a display device 110 operative to present an intelligent contrast warmer user interface, described in more detail in FIG. 4 below. The intelligent contrast warmer user interface may provide information and functions associated with the intelligent contrast warmer. For example, the intelligent contrast warmer user interface may provide inventory, temperature, and contrast expiration information. In another example, the intelligent contrast warmer user interface may provide functions for adding and taking contrast bottles 155, adjusting the temperature, and locking/unlocking the door of the intelligent contrast warmer. In an embodiment, the display device 110 may include a touch screen display device.

As shown in FIG. 1, the intelligent contrast warmer may be in communication with a network 125, including, without limitation, a local area network (LAN), wide area network (WAN), wireless network, and combinations thereof. One or more computing devices may also be connected to the network 125. Illustrative and non-restrictive examples of computing devices may include personal computing devices 130 (e.g., workstations), servers 135 (e.g., data servers, web servers, distributed computing systems (e.g., cloud computing systems), and information systems), mobile computing devices 140 (e.g., tablet computing devices and smart phones), and medical devices 145, such as a contrast injector or contrast holder (described in FIG. 7, below). According to some embodiments, the servers 135 may be part of information systems including, but not limited to, PACS, healthcare information and management systems (HIMS), electronic medical record (EMR) systems, radiology information systems (RIS), contrast information management systems, and medical imaging and procedure equipment information systems (e.g., contrast injector systems). Some embodiments provide that the intelligent contrast warmer, the network, and/or other information systems may be in communication with various other information platforms, such as the Medrad, Inc. Certegra® Informatics Platform. In an embodiment, all of the information and activities associated with an intelligent contrast warmer may be maintained in a database (e.g., a "log") that may be stored within the intelligent contrast warmer system 105. The information and activities may be stored according to relevant regulations (e.g., Joint Commission on Accreditation of Healthcare Organizations (the "Joint Commission" or "TJC") standards require temperature logs to be maintained for at least three years).

One or more information readers 115 may be in communication with the contrast warmer 150, one or more of the networks 125, and/or one or more of the electronic devices 110, 120. An information reader 115 may be configured to read information associated with the contrast bottles 155. For example, each contrast bottle 155 may be associated with one or more labels. Non-restrictive examples of labels include text-based, RFID, barcodes (one dimensional (1D) and/or two-dimensional (2D)), and QR codes. An information reader 115 may be configured to read the information associated with a corresponding type of label. For instance, one information reader 115 may include an RFID reader configured to read RFID labels. In another instance, one information reader 115 may include an OCR reader configured to scan text-based labels and provide text information to one or more information consumers (e.g., the intelligent contrast warmer user interface). Some embodiments provide that information read by the information readers 115 may be transmitted within the contrast warmer system 105. For example, the information from a bottle 155 removed from the contrast warmer 150 for use by a patient having a diagnostic imaging exam may be sent to the intelligent contrast warmer user interface 110, a PACS system, and to the contrast injector 145 that will be used to inject the contrast into the patient. In general, information obtained by an information reader 115 may be generally available for transmission within the intelligent contrast warmer system 105 to electronic devices and computing devices configured to receive and handle the information.

The personal computing devices 130 and mobile computing devices 140 may be used to access information and to perform functions within the intelligent contrast warmer system 105. For example, a personal computing device 130 may be configured to access a user interface (e.g., similar to the intelligent contrast warmer user interface 110) to access information and to perform functions associated with the intelligent contrast warmer 150. In this manner, users may remotely access an intelligent contrast warmer 150 and/or an intelligent contrast warmer user interface 110 associated therewith.

The intelligent contrast warmer user interface 110 may be configured according to some embodiments to provide a user interface for accessing information and to perform functions associated with the intelligent contrast warmer 150. Some embodiments provide that the intelligent contrast warmer user interface 110 may be presented on a display device operatively coupled to a computing device. The computing device may include a processing device and memory. An exemplary processing device 805 and memory 815 are disclosed in reference to FIG. 8. The intelligent contrast warmer user interface 110 may be associated with one or more software applications (e.g., intelligent contrast warmer software application) operative on the computing device to communicate with the intelligent contrast warmer 150 or to communicate with a computing device accessing information associated with the intelligent contrast warmer 150. For instance, the intelligent contrast warmer 150 may include one or more temperature elements for reading the temperature of the intelligent contrast warmer 150 and an electronic locking/unlocking mechanism configured to lock/unlock the door of the intelligent contrast warmer 150. The intelligent contrast warmer user interface 110 may present information and functions associated with the temperature elements and the electronic locking/unlocking mechanism.

According to some embodiments, a user may access information from the intelligent contrast warmer user interface 110 including, but not limited to, contrast warmer temperature information, temperature out-of-range information, contrast bottle inventory information, contrast expiration information, and lock/unlock information. The intelligent contrast warmer user interface 110 may provide user access to one or more functions configured according to some embodiments. Non-restrictive examples of functions include increasing or decreasing the temperature of the intelligent contrast warmer 105, logging into the intelligent contrast warmer system 105, adding a contrast bottle 155, removing a contrast bottle 155, checking the inventory, checking expiration dates, printing labels, transmitting information within the intelligent contrast warmer system 105, and adjusting components of the intelligent contrast warmer 150 (e.g., shelves).

Embodiments provide that the contrast bottles 155 may be associated with one or more labels, described in more detail in reference to FIG. 3 below. Some labels may be generated by the manufacturer and/or supplier of the contrast media or the contrast bottles 145. Some of the labels may be generated by one or more printers 120 arranged within the intelligent contrast warmer system 105. For example, one printer 120 may include an RFID printer configured to print RFID tags that may be affixed to the contrast bottles 145. In another example, one printer 120 may include a text-based printer configured to print text-based labels. The printers 120 and functions associated with the printers 120 may be accessed from the intelligent contrast warmer user interface 110, over the network 125, and combinations thereof.

FIG. 2 depicts an illustrative intelligent contrast warmer configured according to some embodiments. As shown in FIG. 2, an intelligent contrast warmer 205 may include one or more shelves 235 (or racks) arranged to support contrast bottles 255. According to some embodiments, the intelligent contrast warmer 205 may be configured to hold at least fifty contrast bottles 255. The location of the shelves 235 may be manually or automatically adjusted, for example, from an intelligent contrast warmer user interface (e.g., 110 of FIG. 1). The shelves may be automatically adjusted by one or more motors (not shown).

Some embodiments provide for a bottle addition/removal system 215 associated with the intelligent contrast warmer 205. The bottle addition/removal system 215 may be configured so that the bottles 255 may only be placed on a shelf 235 in one direction and removed from a shelf 235 in one direction (e.g., different than the direction for adding the bottles 255). According to some embodiments, the one-way bottle addition/removal system 215 may facilitate a first-in-first-out (FIFO) inventory control system. In FIG. 2, the bottle addition/removal system 215 is configured as a U-shaped channel including two gates 220, 225. Bottles 255 may be added through gate 225, which may only move in one direction (e.g., inward, toward the back of the intelligent contrast warmer 205) to facilitate the addition and to prevent the removal of bottles 255 from this side of the U-shaped channel. Bottles 255 may be removed through gate 220, which may only move in one direction (e.g., outward, toward the front of the intelligent contrast warmer 205) to facilitate the removal and to prevent the addition of bottles 255 from this side of the U-shaped channel. Embodiments are not limited to the U-shaped bottle addition/removal system 215 depicted in FIG. 2 as any bottle addition/removal system capable of facilitating a FIFO inventory control system is contemplated herein. In an embodiment, the contrast bottles 220 may be stored in boxes, such as cardboard boxes holding about 12 bottles, which remain in the intelligent contrast warmer 205 until empty.

The intelligent contrast warmer 205 may be heated by a heating element known to those having ordinary skill in the art. Alternatively, the heating element may comprise an internal heater apparatus 250 configured according to some embodiments to be associated with one or more safeguards to protect the intelligent contrast warmer 205 and contents stored therein.

For example, spills and broken bottles may not affect the internal heater apparatus 250 as it may be contained in a unit separate from the internal area of the intelligent contrast warmer 205 where the bottles 255 are stored. Heat generated by the internal heater apparatus 250 may be circulated within the storage space of the intelligent contrast warmer 205 via one or more circulating fans 230. Some embodiments provide that the internal heater apparatus 250 may include safeguards including, without limitation, an over-temperature shut-off and alert function, measuring the temperature of air going into and returning from the storage space of the intelligent contrast warmer 205, providing a limit on a surface temperature of the internal heater apparatus 250.

A display device 240 may be associated with the intelligent contrast warmer 205. According to some embodiments, the display device 240 may present an intelligent contrast warmer user interface operative to provide user access to intelligent contrast warmer information and functions. The display device 240 may be operatively coupled to a computing device (not shown) configured to run suitable software for accessing information and processing functions accessible from the intelligent contrast warmer user interface. In addition, a basic set of intelligent contrast warmer controls 210 may be accessible from the intelligent contrast warmer 205. In an embodiment, the intelligent contrast warmer controls 210 may include a digital temperature display, buttons for increasing or decreasing the temperature, and a button to stop the heater.

The intelligent contrast warmer 205 may include a lock 245 configured to prevent unauthorized access to the intelligent contrast warmer 205. The lock 245 may be locked/unlocked using electronic signals, biometric devices (e.g., fingerprints), mechanical locking/unlocking methods (e.g., a lock and key mechanism), or some combination thereof. For example, in an embodiment a lock/unlock function may be accessible from the intelligent contrast warmer user interface presented on the display device 240. In this embodiment, a user may select to lock/unlock the intelligent contrast warmer 205 and may be presented with a login user interface for entering security credentials, such as a user name and a password. Responsive to the entry of proper security credentials, the lock/unlock function may operate to cause the transmission of a lock/unlock signal to the lock 245, locking/unlocking the intelligent contrast warmer 205.

Figure 3:
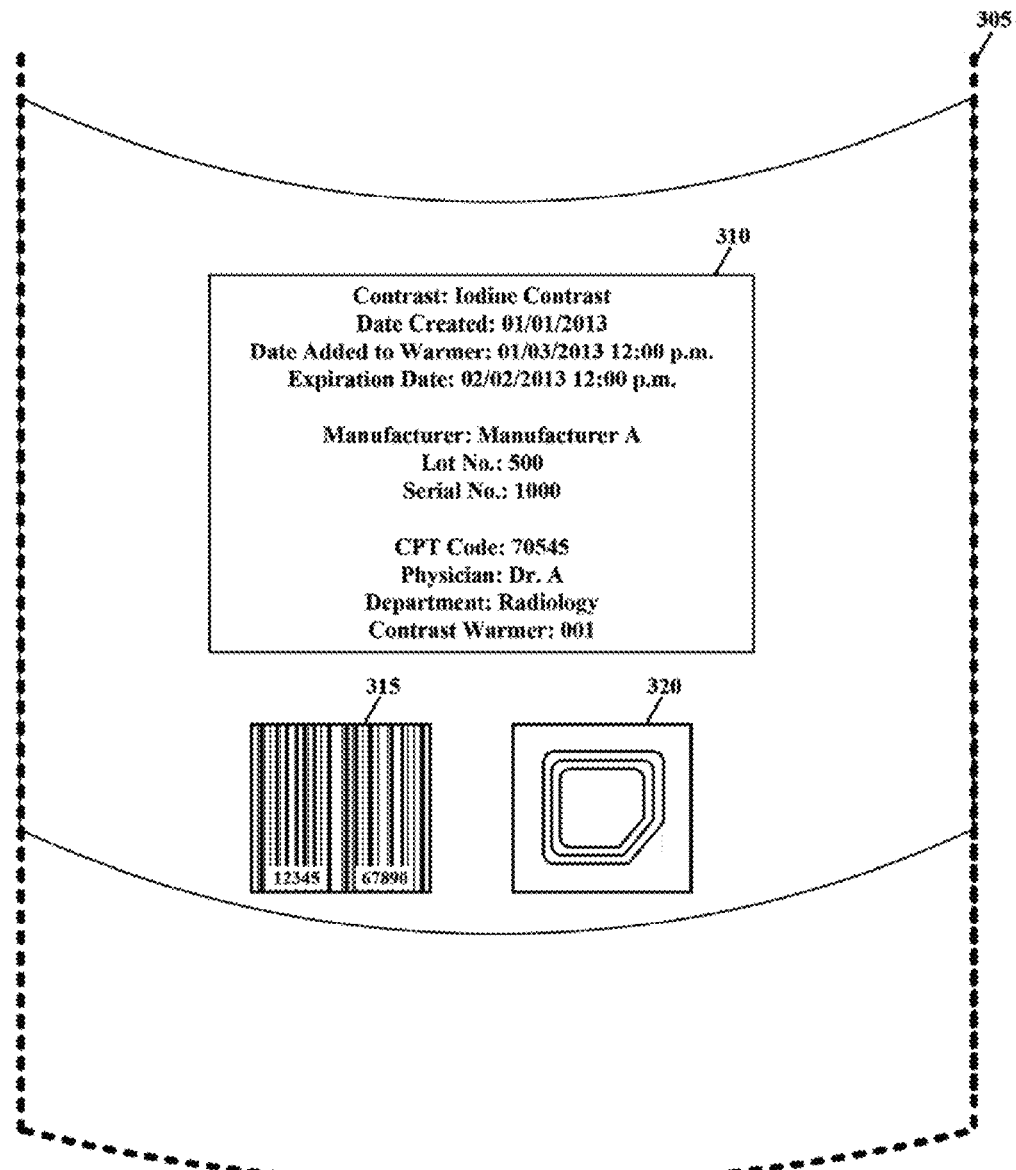
FIG. 3 depicts an illustrative contrast bottle label according to some embodiments.

FIG. 3 depicts an illustrative contrast bottle label according to some embodiments. As shown in FIG. 3, one or more contrast labels 310, 315, 320 may be affixed to a contrast bottle 305 to associate contrast information with the contrast bottle 305. Non-limiting examples of contrast information include type of contrast, concentration, manufacturer, manufacturer instructions, lot number, serial number, creation date, expiration date, date and time added to intelligent contrast warmer, date and time removed from intelligent contrast warmer, temperature of contrast at time of removal, a "do not use after time" indicator (e.g., four hours after removal), hospital information, department information, doctor information, medical procedure information, medical imaging information, automated injection information, intelligent contrast warmer identifier, and current procedural terminology (CPT) number.

Embodiments provide that the contrast information may be included on various types of labels. Illustrative and non-restrictive examples of labels include text-based labels 310, barcode labels 315, or RFID labels 320 or tags. In some embodiments including multiple labels, all or substantially all of the contrast information may be included on each label or, alternatively, certain elements of contrast information may only be associated with certain labels. For instance, contrast manufacturing information (e.g., lot number, date created, etc.) may be associated with the RFID label 320, hospital information (e.g., medical department, diagnostic imaging exam, physician, etc.) may be associated with a text-based label 310, and intelligent contrast warmer information (e.g., date and time added, date and time removed, expiration date, etc.) may be associated with a barcode label 315. Embodiments are not limited to text-based labels 310, barcode labels 315, or RFID labels 320 as depicted in FIG. 3, as any label capable of being associated with contrast information is contemplated herein.

Figure 4:
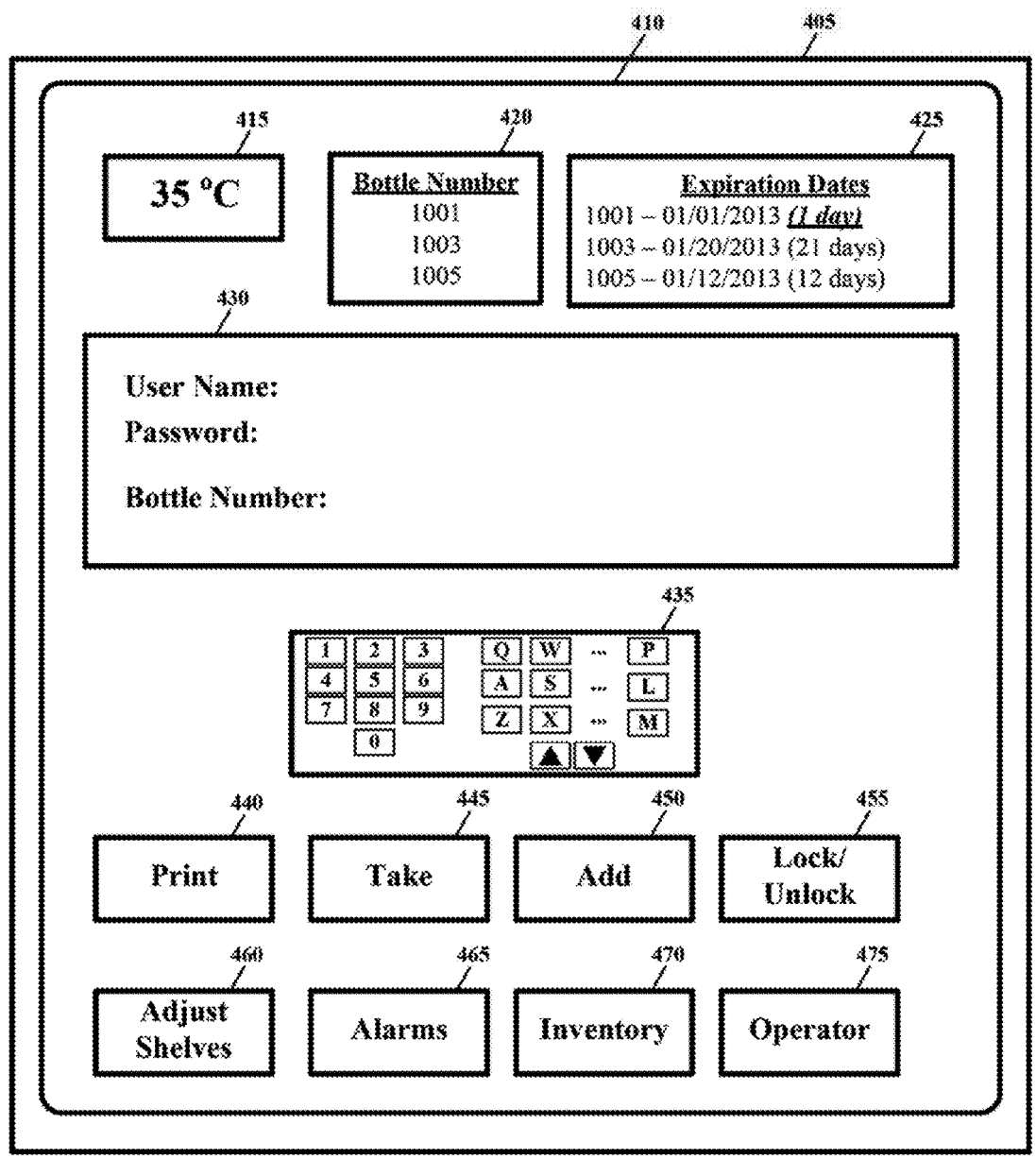
FIG. 4 depicts an illustrative intelligent contrast warmer user interface according to some embodiments.

FIG. 4 depicts an illustrative intelligent contrast warmer user interface according to some embodiments. An intelligent contrast warmer user interface 410 may be presented on a display device 405. Embodiments provide that the display device 405 may be operatively coupled to a computing device running software configured to, inter alia, access information, process user commands, transmit and receive data, and manage the intelligent contrast warmer user interface 410.

According to some embodiments, the software may include intelligent contrast warmer system software including instructions, that when executed on a computing device processor, operate to manage information, communicate with intelligent contrast warmer system electronic and computing devices, process user commands, and execute functions selected from the intelligent contrast warmer user interface 410.

As shown in FIG. 4, the intelligent contrast warmer user interface 410 may include graphical user interface (GUI) elements configured to display information associated with one or more intelligent contrast warmers. For example, the intelligent contrast warmer user interface 410 may display information including intelligent contrast warmer temperatures 415, bottle numbers of bottles stored in the intelligent contrast warmer 420, and expiration dates of the bottles 425. In an embodiment, the GUI elements configured to display information 415, 420, 425 may be configured to differentially display information based on one or more criteria. For instance, if a temperature is outside of specifications, the temperature GUI element 415 may present the temperature in flashing red font. In another instance, if a bottle is within a certain threshold number of days from expiring, the expiration date GUI element 425 may present the expiration date in a different color.

The intelligent contrast warmer user interface 410 may include a data entry GUI element 435 including virtual keys and buttons for data entry, such as alphanumeric keys and symbolic keys. A function window 430 may be configured to provide an interface for information and/or functions associated with the intelligent contrast warmer user interface 410. For example, the function window 430 may provide an interface for entering a user name and password. In another example, the function window 430 may present requested information, such as contrast bottle inventory information. In a further example, the function window 430 may present contrast information for a bottle label scanned by an information reader.

The intelligent contrast warmer user interface 410 may include GUI elements for accessing intelligent contrast warmer and/or intelligent contrast warmer system information and functions. A print GUI element 440 may be configured to allow users to print labels for contrast bottles. Take and add GUI elements 445, 450 may provide functionality for taking bottles from and adding bottles to the intelligent contrast warmer, described in more detail with reference to FIG. 5 and FIG. 6.

A lock/unlock GUI element 455 may initiate a process for locking/unlocking the intelligent contrast warmer. For example, the function window 430 may present a user name and password entry screen responsive to a user selecting the lock/unlock GUI element 455. A user may use the data entry GUI element 435 to enter a user name and password. In an embodiment, the intelligent contrast warmer system may automatically unlock the intelligent contrast warmer responsive to the entry of an authorized user name and password, for example, through unlock signals transmitted by the intelligent contrast warmer system software to the intelligent contrast warmer lock/unlock device.

The location (e.g., height) of intelligent contrast warmer shelves may be adjusted from the intelligent contrast warmer user interface 410 using an adjust shelves GUI element 460. In an embodiment, the function window 430 may present a user interface configured to facilitate movement of the shelves responsive to selection of the adjust shelves GUI element 460. Users may access alarms associated with the intelligent contrast warmer and/or the intelligent contrast warmer system via an alarms GUI element 465. In an embodiment, the function window 430 may present a user interface configured to present alarms responsive to selection of the alarms GUI element 465. Non-limiting examples of alarms include temperature out-of-range conditions, unauthorized access attempts, communication failures, low inventory, expired contrast, and contrast nearing expiration. According to some embodiments, alarms may additionally be communicated within the network electronically, such as through email or short messaging system (SMS) messages.

The inventory of contrast bottles associated with the intelligent contrast warmer may be accessed using an inventory GUI element 470. Some embodiments provide that inventory information may be displayed on the function window 430 responsive to selection of the inventory GUI element 470. Inventory information may include, but is not limited to, the total number of available contrast bottles, expired contrast bottles, contrast bottles nearing expiration, expiration dates of contrast bottles, and types of contrast. The intelligent contrast warmer user interface 410 may include an operator GUI element 475 configured to allow a user to login as an operator of the intelligent contrast warmer user interface 410 and/or the intelligent contrast warmer system. In an embodiment, the operator GUI element 475 may provide a function to associate a physician with a contrast bottle or with an event, such as the removal or addition of a contrast bottle.

In an embodiment, an inventory management system may be configured to manage the contrast bottle inventory associated with the intelligent contrast warmer and/or intelligent contrast warmer system. According to some embodiments, the inventory management system may include software operating on computing devices accessible within the intelligent contrast warmer system.

The inventory management system may track the contrast bottles and contrast information associated therewith. For example, the inventory management system may track bottles added and removed from the intelligent contrast warmer, the length of time that contrast bottles have been stored in the intelligent contrast warmer, record the temperature in the intelligent contrast warmer at predetermined intervals (e.g., about every five minutes, about once an hour, about once a day, etc.), store the temperatures in a database (e.g., a temperature log), and generate alerts related to the contrast bottles and the intelligent contrast warmer. In an embodiment, alerts may be generated when the number of contrast bottles falls below a predetermined threshold, a contrast bottle is returned to the intelligent contrast warmer (against TJC standards), when a contrast bottle is expired (TJC standards specify that contrast may not be left in a contrast warmer for longer than thirty days), and when a contrast bottle is within a predetermined threshold amount of time (e.g., about three days, about two days, about one day, etc.).

In an embodiment, inventory information managed by the inventory management system may be accessed from computing devices associated with the intelligent contrast warmer system and/or networks associated therewith. For example, the inventory information may be stored in a database accessible through the intelligent contrast warmer system. According to some embodiments, a computing device may access inventory information through a website or other web based application. Certain other embodiments provide that the inventory information may be accessed through an application, such as an intelligent contrast warmer system application, client application, or mobile application (e.g., "mobile app" or "app") in communication with the intelligent contrast warmer system and/or other hospital information systems having access to the inventory information.

Figure 5:
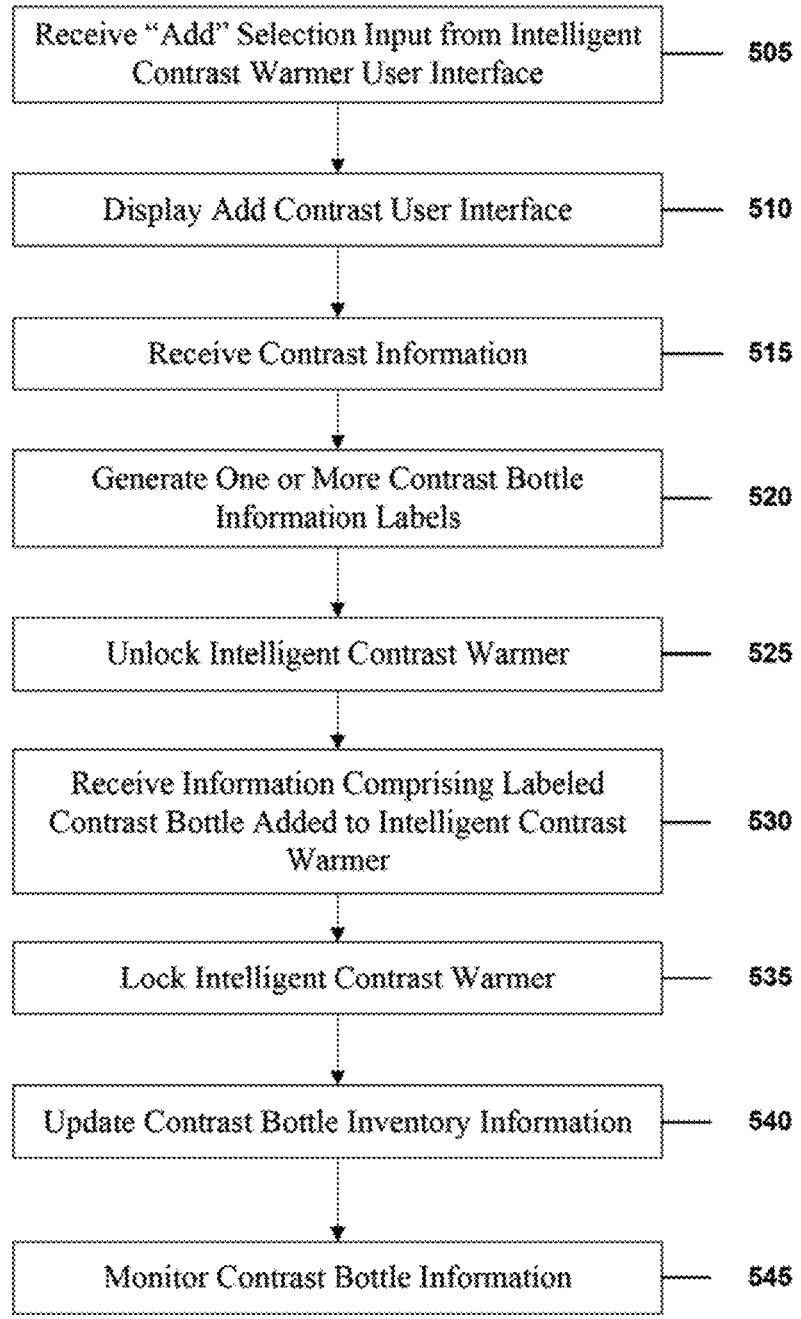
FIG. 5 depicts a flow diagram for an illustrative method for adding a contrast bottle to an intelligent contrast warmer according to some embodiments.

FIG. 5 depicts a flow diagram for an illustrative method for adding a contrast bottle to an intelligent contrast warmer, arranged in accordance with at least some embodiments described herein. The illustrative method of FIG. 5 may be performed, for example, by one or more computing devices 110, 130, 135, 140 depicted in FIG. 1, described above, and/or computing device 800 depicted in FIG. 8 and described in more detail below. In addition, the illustrative method of FIG. 5 may include one or more operations, functions, or actions as illustrated by one or more of blocks 505, 510, 515, 520, 525, 530, 535, 540, and/or 545. The operations described in blocks 505 through 545 may also be stored as computer-executable instructions in a computer-readable medium, such as the system memory 810, 815, 825 of the computing device 800 depicted in FIG. 8. Although illustrated as discrete ordered blocks, various blocks may be divided into additional blocks, combined into fewer blocks, or eliminated, removed, and re-ordered, depending on the desired implementation.

Beginning at block 505, the computing device may receive "add" selection information from the intelligent contrast warmer user interface. For example, the computing device may receive input indicating that a user selected an "add" GUI element on the intelligent contrast warmer user interface.

At block 510, the computing device may present a user interface for adding contrast to the intelligent contrast warmer. For example, an "add contrast" screen may be visible from the intelligent contrast warmer user interface for facilitating the addition of contrast to the intelligent contrast warmer. In an embodiment, the "add contrast" screen may include elements for entering a user name and password, contrast information, and other information associated with adding contrast to the intelligent contrast warmer.

At block 515, the computing device may receive contrast information. For example, a user may scan a label affixed to the contrast bottle using an information reader communicatively coupled to the computing device (e.g., directly, through a network, etc.). In another example, a user may manually enter all or part of the contrast information associated with the contrast bottle using data entry components of the intelligent contrast warmer user interface. In a further example, a user may access contrast information from a database or other information store for transmission to the computing device. The contrast information transmitted to the computing device may be associated with the contrast bottle and displayed on the intelligent contrast warmer user interface.

In an embodiment, the computing device may operate to generate an alarm if it determines (e.g., via an intelligent contrast warmer software application) that a user is attempting to re-stock contrast previously removed from the intelligent contrast warmer or is attempting to add expired contrast. The computing device may determine the status of a contrast bottle based on the received contrast information. In another embodiment, the computing device may initiate processes to prevent the re-stocking of contrast and/or the addition of expired or nearly expired contrast (e.g., expiring within a threshold number of days based on date of manufacture), including, without limitation, locking the door, logging out the user, and disabling label printing.

At block 520, the computing device may generate one or more contrast labels. For example, selection of a "print" function from the intelligent contrast warmer user interface may send the contrast information to one or more printers in communication with the computing device and/or a network accessible from the computing device. The printers may print labels including some or all of the contrast information. For instance, an RFID printer may print an RFID label including contrast information specified for an RFID label, a barcode printer may print a barcode label including contrast information specified for a barcode label, a text-based printer may print a text-based label including contrast information specified for a text-based label, and combinations thereof.

At block 525, the computing device may facilitate the unlocking of the intelligent contrast warmer. For example, the intelligent contrast warmer user interface may provide a user interface for unlocking the intelligent contrast warmer. The user interface for unlocking the door may display user name, password, and unlocking elements (e.g., intelligent contrast warmer selection, confirm unlock, etc.).

At block 530, the computing device may receive information indicating that a contrast bottle has been added to the intelligent contrast warmer. For example, the user may enter a selection at the intelligent contrast warmer user interface confirming that a bottle has been added to the intelligent contrast warmer. In another example, the computing device may automatically receive information from the intelligent contrast warmer indicating that a contrast bottle has been added, such as from an electronic device configured to perceive the addition of contrast bottles to the intelligent contrast warmer user interface. For instance, the electronic device may include an electronic eye or scale device in communication with the computing device.

At block 535, the computing device may facilitate the locking of the intelligent contrast warmer. For example, the intelligent contrast warmer user interface may provide a user interface for locking the intelligent contrast warmer. The user interface for locking the door may display user name, password, and unlocking elements (e.g., intelligent contrast warmer selection, confirm unlock, etc.). In another example, the intelligent contrast warmer may automatically lock when closed without intervention from the computing device. In this example, the intelligent contrast warmer user interface may receive information that the door is closed from an electronic locking mechanism used to lock the door.

At block 540, the computing device may update the contrast bottle inventory information. For example, the contrast information for the bottle added to the intelligent contrast warmer may be added to a database or other data repository accessible by the computing device. In an embodiment, the inventory information may be transmitted to an inventory management system as described herein.

At block 545, the computing device may monitor contrast bottle information. For example, the intelligent contrast warmer system application may operate to monitor information including intelligent contrast warmer temperatures, contrast bottle inventory, and expiration dates. The information may be used within intelligent contrast warmer system to facilitate compliance with intelligent contrast warmer operational standards (e.g., TJC).

Figure 6:
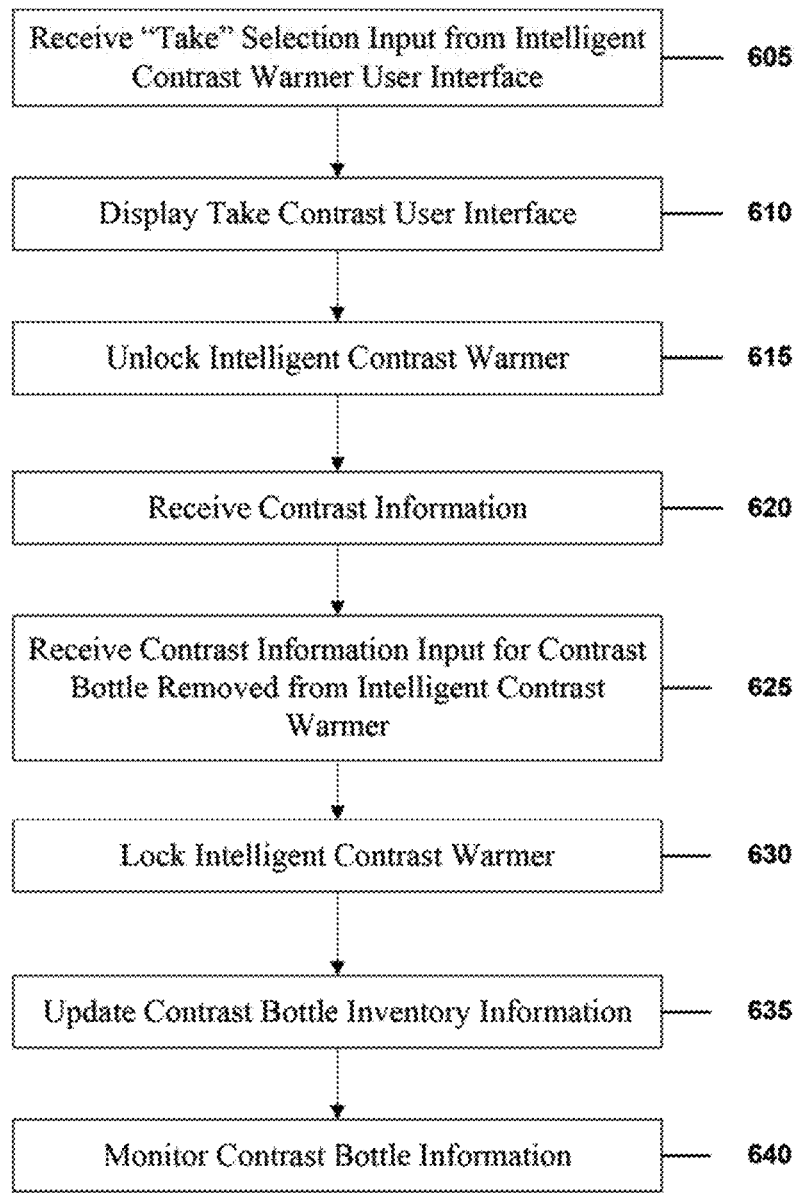
FIG. 6 depicts a flow diagram for an illustrative method for taking a contrast bottle from an intelligent contrast warmer according to some embodiments.

FIG. 6 depicts a flow diagram for an illustrative method for removing a contrast bottle from an intelligent contrast warmer, arranged in accordance with at least some embodiments described herein. The illustrative method of FIG. 6 may be performed, for example, by one or more computing devices 110, 130, 135, 140 depicted in FIG. 1, described above, and/or computing device 800 depicted in FIG. 8 and described in more detail below. In addition, the illustrative method of FIG. 6 may include one or more operations, functions, or actions as illustrated by one or more of blocks 605, 610, 615, 620, 625, 630, 635, and/or 640. The operations described in blocks 605 through 640 may also be stored as computer-executable instructions in a computer-readable medium, such as the system memory 810, 815, 825 of the computing device 800 depicted in FIG. 8. Although illustrated as discrete ordered blocks, various blocks may be divided into additional blocks, combined into fewer blocks, or eliminated, removed, and re-ordered, depending on the desired implementation.

Beginning at block 605, the computing device may receive "take" selection information from the intelligent contrast warmer user interface. For example, the computing device may receive input indicating that a user selected a "take" GUI element on the intelligent contrast warmer user interface.

At block 610, the computing device may present a user interface for taking contrast from the intelligent contrast warmer. For example, a "take contrast" screen may be visible from the intelligent contrast warmer user interface for facilitating the removal of contrast from the intelligent contrast warmer. In an embodiment, the "take contrast" screen may include elements for entering a user name and password, contrast information, and other information associated with removing contrast from the intelligent contrast warmer.

At block 615, the computing device may facilitate the unlocking of the intelligent contrast warmer. For example, the intelligent contrast warmer user interface may provide a user interface for unlocking the intelligent contrast warmer. The user interface for unlocking the door may display user name, password, and unlocking elements (e.g., intelligent contrast warmer selection, confirm unlock, etc.).

At block 620, the computing device may receive contrast information. For example, a user may scan a label affixed to the contrast bottle using an information reader communicatively coupled to the computing device (e.g., directly, through a network, etc.). In another example, a user may manually enter all or part of the contrast information associated with the contrast bottle using data entry components of the intelligent contrast warmer user interface. In a further example, a user may access contrast information from a database or other information store for transmission to the computing device. In a still further example, all or part of the contrast information may be obtained based on the order that the contrast bottle was added to a FIFO intelligent contrast warmer. As the intelligent contrast warmer system monitors contrast bottle inventory, the intelligent contrast warmer system may keep track of the position of the bottles within a FIFO intelligent contrast warmer based on the order they were added to the intelligent contrast warmer. The contrast information transmitted to the computing device may be associated with the contrast bottle.

At block 625, the computing device may receive information indicating that a contrast bottle has been removed from the intelligent contrast warmer. For example, the user may enter a selection at the intelligent contrast warmer user interface confirming that a bottle has been removed from the intelligent contrast warmer. In another example, the computing device may automatically receive information from the intelligent contrast warmer indicating that a contrast bottle has been removed, such as from an electronic device configured to perceive the removal of contrast bottles from the intelligent contrast warmer user interface. For instance, the electronic device may include an electronic eye or scale device in communication with the computing device.

At block 630, the computing device may facilitate the locking of the intelligent contrast warmer. For example, the intelligent contrast warmer user interface may provide a user interface for locking the intelligent contrast warmer. The user interface for locking the door may display user name, password, and unlocking elements (e.g., intelligent contrast warmer selection, confirm unlock, etc.). In another example, the intelligent contrast warmer may automatically lock when closed without intervention from the computing device. In this example, the intelligent contrast warmer user interface may receive information that the door is closed from an electronic locking mechanism used to lock the door.

At block 635, the computing device may update the contrast bottle inventory information. For example, the contrast information for the bottle removed from the intelligent contrast warmer may be added to a database or other data repository accessible by the computing device. In an embodiment, an inventory management system may be configured to manage the contrast bottle inventory associated with the intelligent contrast warmer and/or intelligent contrast warmer system.

At block 640, the computing device may monitor contrast bottle information. For example, the intelligent contrast warmer system application may operate to monitor information including intelligent contrast warmer temperatures, contrast bottle inventory, and expiration dates. The information may be used within intelligent contrast warmer system to facilitate compliance with intelligent contrast warmer operational standards (e.g., TJC).

After the contrast bottle has been removed from the intelligent contrast system, the user may use the contrast with various other systems. For example, the contrast bottle may be used with an automated contrast injector system. The contrast information may be obtained from the contrast bottle label, such as through an information reader, manual data entry, or accessed through the intelligent contrast warmer system or other information system. The contrast information may then be used to improve the delivery or quality of patient care. For instance, the contrast information may be added to a patient record, used to check for patient allergies and/or contradictions, used to make a pressure selection or flow rate selection for an automated contrast injection system, used to adjust procedural protocols, such as the personalized patient protocol technology (P3T®) developed by Medrad Inc. for the accurate, personalized delivery of contrast during CT exams.

Figure 7:
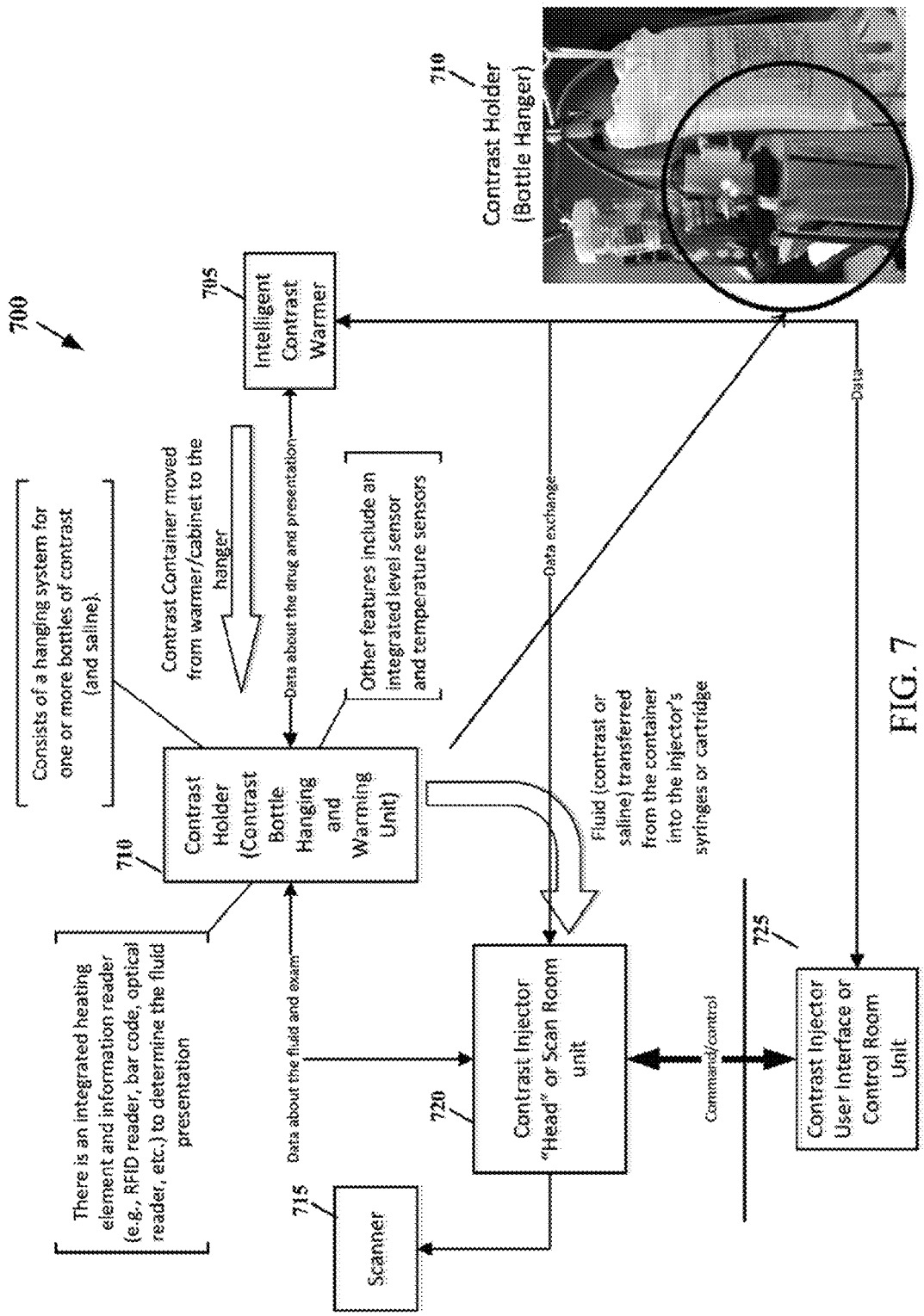
FIG. 7 depicts an illustrative contrast holder according to some embodiments.

FIG. 7 depicts an illustrative contrast holder configured according to some embodiments. As shown in FIG. 7, an intelligent contrast warmer system 700 may comprise a contrast holder 710 configured to hold contrast being used for a medical procedure, such as a diagnostic exam. As such, the contrast holder 710 may be situated near a patient in an exam room. In a non-limiting example, the contrast holder 710 may be configured in a bottle hanger arrangement that holds a bottle of contrast connected to an injector such that the contrast holder may be in fluid communication with an injector 720, such as the syringe or cartridge of an automatic injector system. In this manner, a bottle of contrast or the contents thereof may be obtained from an inventory of contrast, such as contrast stored in a contrast warmer 705, and placed into the contrast holder 710. The contrast may then be delivered to a patient through a manual or automatic injection process.

According to some embodiments, a saline (not shown) container may additionally be warm and hung in the contrast holder 710. In an embodiment, the saline container may comprise an ID tag, which may be utilized for identification and/or tracking purposes.

In FIG. 7, the contrast holder 710 is in communication with a health information system or other network, such as the network 125 depicted in FIG. 1. The contrast holder 710 may obtain information about the contrast stored therein from the health information network, including information associated with the contrast warmer 705 according to embodiments described herein. Illustrative information includes data about the contrast (or other drug) and presentation (e.g., packaging) information. In an embodiment, the contrast holder 710 may comprise one or more sensors, for example, sensors that may operate to provide information about the contrast bottle or contrast stored therein. For instance, the sensors may include level sensors and temperature sensors. The contrast holder 710 may have an integrated heating element to heat contents stored therein and an information reader, such as an RFID reader, to scan information from a label affixed to the contrast bottle as described according to embodiments herein.

According to some embodiments, the intelligent contrast warmer system 700 and components thereof (e.g., the contrast holder 710, contrast warmer 705, etc.) may receive data from an injection system, such as injector 720. Illustrative data includes, but is not limited to, actual amount of contrast and/or saline delivered, patient information, adverse events, and other data associated with operation of the injector.

As shown in FIG. 7, a contrast injector user interface or control room unit 725 may be provided for command and control functions of the intelligent contrast system 700, such as the contrast injector "head"/scan room unit 720. For example the contrast injector user interface or control room unit 725 may provide functions to start injection of the contents of the contrast holder 710 or to check the temperature of the contents of the contrast holder.

The contrast injector user interface or control room unit 725 may be in communication with a scanner 715, such as a CT scanner, operating to perform a medical diagnostic exam. Through the network (e.g., network 125 of FIG. 1, a local network, a direct communication link, or a combination thereof) the contrast holder 710 may receive information about the fluid and the exam, for example, from the contrast injector user interface or control room unit 725, the scanner 715, or a health information network (e.g., through a patient record) in communication therewith.

Figure 8:
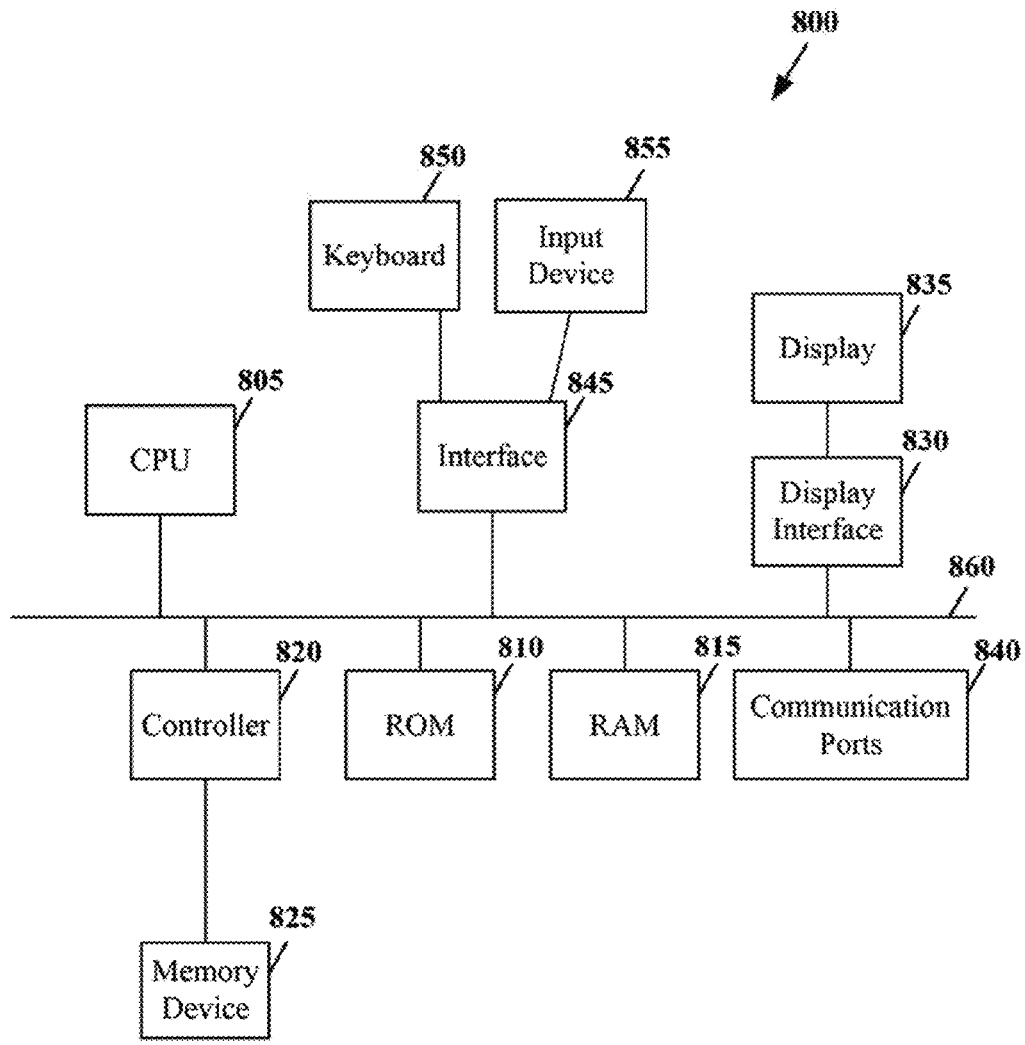
FIG. 8 depicts illustrative computing device internal hardware according to some embodiments.

FIG. 8 depicts illustrative computing device internal hardware according to some embodiments that may be used to contain or implement program instructions, such as the process steps discussed above in reference to FIG. 5 and FIG. 6, according to embodiments. The computing device 800 may include a bus 860 that serves as the main information highway interconnecting the other illustrated components of the hardware. CPU 805 is the central processing unit of the system, performing calculations and logic operations required to execute a program. CPU 805, alone or in conjunction with one or more of the other elements disclosed in FIG. 8, is an exemplary processing device, computing device or processor as such terms are used within this disclosure. Read only memory (ROM) 810 and random access memory (RAM) 815 constitute exemplary memory devices (i.e., processor-readable non-transitory storage media).

A controller 820 interfaces with one or more optional memory devices 825 to the system bus 860. These memory devices 825 may include, for example, an external or internal DVD drive, a CD ROM drive, a hard drive, flash memory, a USB drive or the like. As indicated previously, these various drives and controllers are optional devices.

Program instructions, software or interactive modules for providing the interface and performing any querying or analysis associated with one or more data sets may be stored in the ROM 810 and/or the RAM 815. Optionally, the program instructions may be stored on a tangible computer readable medium such as a compact disk, a digital disk, flash memory, a memory card, a USB drive, an optical disc storage medium, such as a Blu-ray™ disc, and/or other non-transitory storage media.

An optional display interface 830 may permit information from the bus 860 to be displayed on the display 835 in audio, visual, graphic or alphanumeric format. Communication with external devices, such as a print device, may occur using various communication ports 840. An exemplary communication port 840 may be attached to a communications network, such as the Internet or an intranet.

The hardware may also include an interface 845 which allows for receipt of data from input devices such as a keyboard 850 or other input device 855 such as a mouse, a joystick, a touch screen, a remote control, a pointing device, a video input device and/or an audio input device.

Without further analysis, the foregoing will so fully reveal the substance of these embodiments that others can, by applying current knowledge, readily adapt it for various applications without omitting features that, from the standpoint of prior art, fairly constitute characteristics of the generic or specific aspects of the embodiments disclosed herein.

If not otherwise stated herein, it may be assumed that all components and/or processes described heretofore may, if appropriate, be considered to be interchangeable with similar components and/or processes disclosed elsewhere in the specification, unless an express indication is made to the contrary.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the disclosed embodiments.

What is claimed is:

1. A contrast warmer configured to warm contrast bottles stored therein, the contrast warmer comprising:
   a temperature sensor operative to measure a temperature of the contrast warmer;
   an information reader operative to read contrast information of a contrast label affixed to at least one contrast bottle, the contrast information comprising an expiration time; and
   a communications port in operative communication with at least one computing device configured to monitor the temperature and the expiration time,
   wherein an alarm event is generated by the at least one computing device responsive to at least one of the temperature being outside of an acceptable temperature range and a current time being within a threshold duration of the expiration time, and
   wherein a record of the alarm event is stored in a database accessible by the at least one computing device.

2. A method of monitoring an expiration time of a contrast bottle stored in a contrast warmer, the method comprising:
   affixing a contrast label to the contrast bottle, the contrast label comprising the expiration time of the contrast bottle;
   reading the expiration time from the contrast label using an information reader;
   placing the contrast bottle in the contrast warmer;
   communicating the expiration time from the information reader to at least one computing device configured to receive the expiration time;
   generating, by the at least one computing device, an alarm event responsive to a current time being within a threshold duration of the expiration time; and
   storing a record of the alarm event in a database accessible by the at least one computing device.

3. The method of claim 2, wherein the threshold duration comprises at least twenty-four hours.

4. A contrast warmer system comprising:
a fluid injector configured to inject contents of a contrast bottle into a patient; and
a contrast holder comprising:
a heating element configured to store and warm the contrast bottle,
an information reader configured to read contrast information from a contrast label affixed to the contrast bottle, and
a communication port configured to enable two-way communication with the fluid injector,
wherein the contrast holder is in fluid communication with the fluid injector,
wherein the contrast holder is configured to send the contrast information to the fluid injector, and
wherein the contrast holder is configured to receive injection information from the fluid injector.

5. The contrast warmer system of claim 4, wherein the contrast holder comprises a bottle hanger configured to hold the contrast bottle.

6. The contrast warmer system of claim 4, wherein the contrast holder comprises an integrated level sensor.

7. The contrast warmer system of claim 4, wherein the contrast holder comprises a temperature sensor.

8. The contrast warmer system of claim 4, wherein the contrast warmer system is in communication with a network.

9. The contrast warmer of claim 1, further comprising a user interface in operative communication with the at least one computing device, the user interface configured for controlling operation of the contrast warmer.

10. The contrast warmer of claim 1, further comprising a contrast bottle management system based on a first-in-first-out inventory control system.

11. The contrast warmer of claim 10, wherein the contrast bottle management system has a channel having a first one-way input gate and a second one-way output gate.

12. The contrast warmer of claim 11, wherein the contrast bottles move in one direction through the channel.

13. The contrast warmer of claim 1, further comprising at least one manually or automatically adjustable shelf.

14. The contrast warmer of claim 1, further comprising at least one lock configured to prevent unauthorized access to the contrast warmer.

15. The contrast warmer system of claim 4, wherein the contrast information includes patient information and wherein the injection information includes data associated with operation of the fluid injector.

16. The contrast warmer system of claim 4, further comprising a user interface configured for controlling operation of the contrast warmer system.

17. The contrast warmer system of claim 4, wherein the contrast holder is configured for receiving the contrast information from a health information network.

18. The contrast warmer system of claim 17, wherein the contrast information includes data about the contents of the contrast bottle.

* * * * *

UNITED STATES PATENT AND TRADEMARK OFFICE
CERTIFICATE OF CORRECTION

| | |
|---|---|
| PATENT NO. | : 9,080,707 B2 |
| APPLICATION NO. | : 13/765467 |
| DATED | : July 14, 2015 |
| INVENTOR(S) | : Kohler et al. |

It is certified that error appears in the above-identified patent and that said Letters Patent is hereby corrected as shown below:

IN THE SPECIFICATION:

In Column 1, Line 43, delete "TX" and insert -- TJC --, therefor.

In Column 7, Line 39, delete "contrast bottles 220" and insert -- contrast bottles 255 --, therefor.

Signed and Sealed this
Fifteenth Day of December, 2015

Michelle K. Lee
*Director of the United States Patent and Trademark Office*